United States Patent [19]

Klingler et al.

[11] 4,150,227
[45] Apr. 17, 1979

[54] PROCESS FOR THE PRODUCTION OF BASIC SUBSTITUTED ALKYL THEOPHYLLINE

[75] Inventors: Karl-Heinz Klingler, Langen; Erich Bickel, Frankfurt am Main, both of Fed. Rep. of Germany

[73] Assignee: Deutsche Gold- und Silber-Scheideanstalt vormals Roessler, Frankfurt am Main, Fed. Rep. of Germany

[21] Appl. No.: 862,977

[22] Filed: Dec. 21, 1977

[30] Foreign Application Priority Data

Jan. 17, 1977 [DE] Fed. Rep. of Germany ....... 2701629

[51] Int. Cl.² ........................................... C07D 473/08
[52] U.S. Cl. ..................................... 544/272; 424/253
[58] Field of Search ............................... 544/256, 272

[56] References Cited
U.S. PATENT DOCUMENTS

| 3,398,150 | 4/1968 | Klinger et al. | 260/256 |
| 3,728,346 | 4/1973 | Klingler | 260/256 |

FOREIGN PATENT DOCUMENTS 1545725 1/1965 Fed. Rep. of Germany.
2136643 7/1971 Fed. Rep. of Germany.

*Primary Examiner*—Nicholas S. Rizzo
*Attorney, Agent, or Firm*—Cushman, Darby & Cushman

[57] ABSTRACT

Basic substituted alkyl theophylline derivatives of the formula

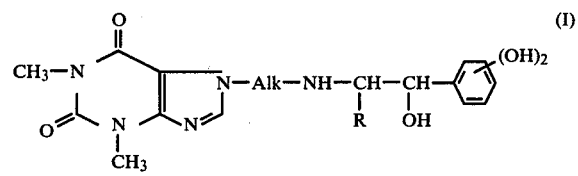

in which Alk is a straight or branched chain alkylene group with 2 to 4 carbon atoms and R is hydrogen or a methyl group are produced by catalytic hydrogenation of compounds of the formula

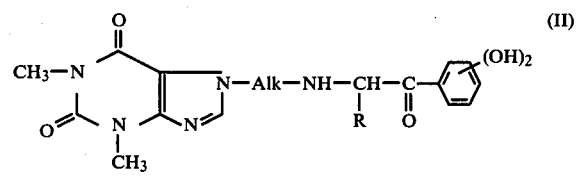

where the phenolic hydroxyl groups and/or the secondary basic nitrogen atom can contain protective groups using as the solvent a compound of the formula

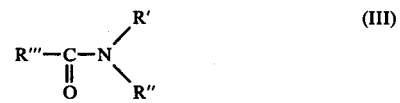

where R', R" and R''' are the same or different and are alkyl groups of 1 to 2 carbon atoms and R' together with R''' can also be an alkylene bridge with 3 to 4 carbon atoms and in a given case the protective groups present are split off.

21 Claims, No Drawings

PROCESS FOR THE PRODUCTION OF BASIC SUBSTITUTED ALKYL THEOPHYLLINE

BACKGROUND OF THE INVENTION

German Pat. No. 1,545,725 (and related but not identical Klingler U.S. Pat. No. 3,398,150) as well as German OS No. 2 136 643 (and related Klingler U.S. Pat. No. 3,728,346) among other matters disclose a process for the production of compounds of the general formula

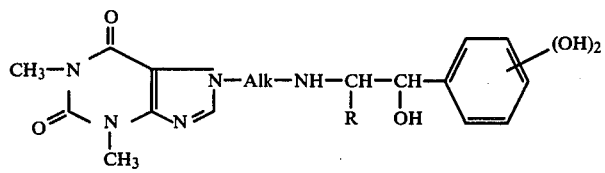

wherein Alk is a straight or branched chain alkylene group with 3 to 4 carbons and R is hydrogen or an alkyl group with 1 to 6 carbon atoms by catalytic hydrogenation of ketones of the general formula

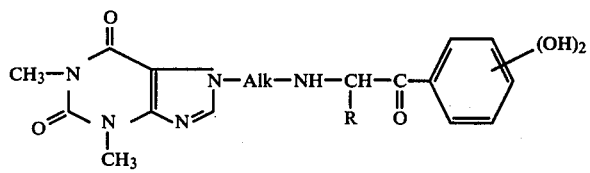

wherein the phenolic hydroxyl groups and/or the basic secondary nitrogen atoms can be protected by a benzyl.

The entire disclosures of the two Klingler United States patents are hereby incorporated by reference and relied upon.

The hydrogenation is carried out in water, methanol, ethanol or water-alcohol mixture.

A great disadvantage in the hydrogenation of such compounds, however, is that it is necessary to work in great dilution since the starting ketones have extremely low solubility. If, for example, there is used a starting ketone of formula (B) in which the secondary basic nitrogen atom has a benzyl group as a protective group, in the hydrogenation first this benzyl group is split off so that the nearly insoluble ketone which is formed very frequently precipitates out in the reaction vessel even at elevated temperatures and high dilutions and the catalyst surface is thereby so inactivated that then the already only difficultly hydrogenatable keto group is only reduced extremely slowly and incompletely. The described disadvantages are particularly noticeable in technical and production scale operations.

As can be seen, for example, from German Pat. No. 1,545,725 in the hydrogenation of ketones of formula (B) (Examples 1, 2, 6 and 7) there is needed 25 to 72 times the amount of solvents in the form of mixtures. Even if there should be used dimethyl formamide (not disclosed in the German patent) which is exceptionally suitable for catalytic hydrogenation of difficultly soluble substances the preliminary product of Example 2, for example, must be dissolved in 15 times the amount of this solvent. However, at the optimum temperatures of 60° to 70° C. for this reaction there precipitates out under these conditions the debenzylated ketone (B) as a result of which the further hydrogenations, particularly in large scale operations, becomes extremely difficult. In the necessary hydrogenation times of about 48 hours there arise colored by-products and the still strongly ketone containing final product formed must be post hydrogenated to obtain the required purity for pharmaceutical use and must be recrystallized with attendant substantial loss of product. A large scale production in this manner therefore is very expensive and uneconomical.

SUMMARY OF THE INVENTION

The invention is directed to a process for the production of basic substituted alkyl theophylline derivatives (A)

(B)

of the formula

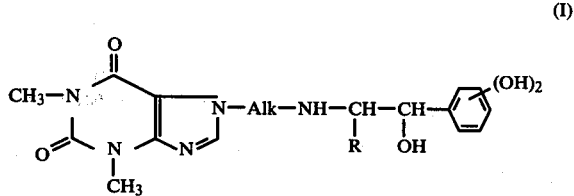
(I)

in which Alk is a straight or branched chain alkylene group with 2 to 4 carbon atoms and R is hydrogen or a methyl group by catalytic hydrogenation of compounds of the formula

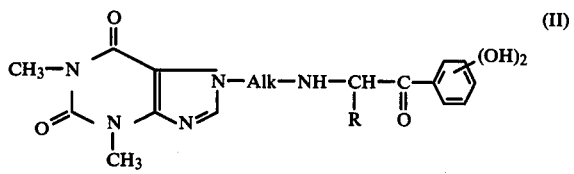
(II)

where Alk and R are defined as above and where the phenolic hydroxyl group and/or the secondary basic nitrogen atom can contain protective groups and is characterized by the hydrogenation taking place in a solvent of the formula

(III)

where R', R" and R''' are the same or different and are alkyl groups of 1 to 2 carbon atoms and wherein R' together with R''' can also form an alkylene bridge with 3 to 4 carbon atoms.

In the event that the reaction product still contains protective groups these can be split off in the customary manner for this purpose.

In formulae (I) and (II) Alk especially can be the following groups:

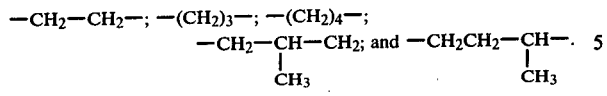

Examples of compounds of formula (I) which can be prepared from the corresponding compounds of formula (II) include:

7-{3-[2-(3,5-dihydroxyphenyl)-2-hydroxyethylamino]-propyl}-theophylline;
7-{2-[2-(3,4-dihydroxyphenyl)-2-hydroxyethylamino]-ethyl}-theophylline;
7-{3-[2-(2,4-dihydroxyphenyl)-2-hydroxyethylamino]-butyl-(1)}-theophylline;
7-{2-methyl-3-[2-(3,5-dihydroxyphenyl)-2-hydroxyethylamino]-propyl-(1)}-theophylline;
7-{2-methyl-3-[2-(2,4-dihydroxyphenyl)-2-hydroxyethylamino]-propyl-(1)}-theophylline;
7-{3-[2-(3,5-dihydroxyphenyl)-2-hydroxyethylamino]-butyl-(1)}-theophylline;
7-{3-[2-(3,4-dihydroxyphenyl)-2-hydroxyethylamino]-butyl-(1)}-theophylline;
7-{3-[2-(3,5-dihydroxyphenyl)-1-methyl-2-hydroxyethylamino]-propyl-(1)}-theophylline;
7-{2-methyl-3-[1-methyl-2-(3,4-dihydroxyphenyl)-2-hydroxyethylamino]-propyl-(1)}-theophylline;

The starting compounds of formula (II) can be employed in the form of the free base or as the acid addition salt, e.g., as the salts of any non toxic pharmaceutically acceptable acid such as hydrochloric acid, hydrobromic acid, sulfuric acid, p-toluene sulfonic acid, acetic acid, propionic acid, succinic acid, maleic acid, gluconic acid, malonic acid, fumaric acid, lactic acid, tartaric acid, citric acid or phosphoric acid, for example.

It is surprising that the difficulties described above do not occur if the hydrogenation is carried out in a solvent of formula (III). In the case where R' and R'" of formula (III) together form an alkylene bridge with 3 or 4 carbon atoms the formula in this case becomes

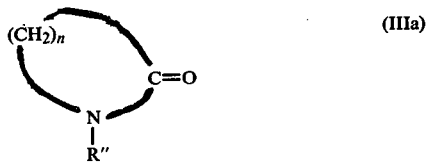

where n is 3 or 4 and R" is $CH_3$ or $C_2H_5$.

Examples of solvents within formula (III) [including formula (IIIa)] are dimethyl acetamide, diethyl acetamide, dimethyl propionamide, diethyl propionamide, N-methyl pyrrolidone, N-ethyl pyrrolidone, N-methyl piperidone and N-ethyl piperidone.

The preferred solvents of the described structure are dimethyl acetamide and N-methyl pyrrolidone. There are also usable mixtures of these commercial solvents with water wherein the portion of water is not over 50%. For example, there can be a water portion up to 30% with either N-methyl pyrrolidone or dimethyl acetamide. Preferably the water portion is 0 to 10%.

According to the process of the invention the ketone of general formula (II) is usually dissolved in 5 to 15 times the amount of a solvent of formula (III) and after addition of the hydrogenation catalyst is hydrogenated at temperatures between 20° and 100° C. The reaction can be carried out under pressure (for example, up to 50 bar, preferably 2-10 bar) or without superatmospheric pressure. In the event that in any hydrogenation the take up of hydrogen is strongly reduced as sometimes occurs through the presence of traces of catalyst poisons, the composition can be filtered and after addition of fresh catalyst the hydrogenation completed. This is not possible in the prior art processes since the starting ketone precipitated out in the retardation of the reaction cannot be separated from the catalyst in a simple manner. To work up the product there suffices concentration of the filtered hydrogenation solution in a vacuum and purification of the residue by customary methods such as recrystallization, dissolving and precipitating or boiling with a solvent, preferably with alcohol. The recovery of the solvent in the concentration of the reaction solution is readily possible since the toluene formed in the hydrogenation of benzyl protective group containing starting ketones is easily separated off (due to the high difference in boiling point between toluene and the solvents used in the invention).

The reduction according to the process of the invention takes place by means of catalytically activated hydrogen using conventional metal catalysts which are used for the reduction of an oxo group to a hydroxyl group. The catalysts can be used with and without carriers. Especially suited are noble metal catalysts such as palladium (for example, palladium-carbon or palladium on barium sulfate), platinum and platinum oxide.

The reduction of the keto group can also be accomplished in other ways, for example, by lithium aluminum hydride or sodium borohydride.

Hydrogenolytically splittable protective groups present are generally split off in the reduction in the event that this takes place with hydrogen in the presence of palladium catalysts. In the event that protective groups present are not split off during the reaction then these can be removed, for example, after the end of the reduction of the oxo group by treatment with hydrogen in the presence of a palladium catalyst or they can be removed by customary hydrolysis.

In the process of the invention it is frequently suitable to protect the phenolic hydroxyl groups as well as the secondary amino group by known protective groups. Frequently such protective groups are already required for the production of the starting compound. These protective groups are easily split off from the final product. There are used either easily solvolytically splittable acyl groups or groups splittable upon hydrogenation, as for example, the benzyl groups. The solvolytically splittable protective groups are split off, for example, by deesterification or saponification with dilute acids, e.g., dilute hydrochloric acid or sulfuric acid, at room temperature or with a short heating, e.g., boiling. Depending on the type of protective group, however, the splitting off already takes place during the reaction process. The latter is the case, for example, if the secondary amino group as well as, in a given case, also the phenolic hydroxy groups are protected by a benzyl group or the carbobenzoxy radical and a palladium catalyst is used. If the protective group is not split off during the reaction there is required a simple post treatment of the reaction product wherein the splitting off of the protective group or groups takes place, for example, under conditions such as those stated above.

As protective groups for the secondary amino groups there can be used, for example, the benzyl group, α-phenylethyl group, trityl group, benzyl groups substituted in the benzene nucleus as for example the p-bromobenzyl group or the p-nitrobenzyl group; hydroxycarbonyl groups such as the carbobenzoxy group, the carbobenzthio group or the tert-butyl hydroxycarbonyl group; the trifluoroacetyl group, the phthalyl group, tert.-butylcarboxy group, the p-toluenesulfonyl group and similar groups. These same protective groups can be used for the phenolic hydroxyl groups; additionally there can be used also simple acyl groups as for example lower alkanoyl groups such as the acetyl group, formyl group, propionyl group or butyryl group or lower carbalkoxy groups, e.g., carbomethoxy, carboethoxy, carbopropoxy or carbobutoxy.

In summary the essential advantages of the new process compared to the known processes are:
1. Insoluble intermediate products do not precipitate out during the reaction.
2. Higher yields (for example, 94.5% instead of 66.5% according to Example 2 of German Pat. No. 1,545,725).
3. Shorter hydrogenation time.
4. Higher concentrations. In connection therewith there are possible considerably higher charges in the same reaction vessel whereby there are saved solvent and fabrication costs.
5. There are no difficulties in employing large quantities of materials.
6. The working up is simpler than was possible previously.
7. There is obtained higher purity of the end product.
8. The recovery of the solvent is simpler.

Unless otherwise indicated all parts and percentages are by weight.

The process can comprise, consist essentially of or consist of the steps set forth and the compositions used can comprise, consist essentially of or consist of the materials set forth.

DESCRIPTION OF THE PREFERRED EMBODIMENTS

EXAMPLE 1

500 grams of 7-{3-[2-(3,5-dihydroxyphenyl)-2-oxoethyl-benzylamino]-propyl}-theophylline hydrochloride were dissolved in 5 liters of dimethyl acetamide. There were added 25 grams of a 10% palladium-carbon catalyst, the mixture heated to 70° C. and hydrogenated with stirring at this temperature and 2 bar pressure until the speed of hydrogenation perceptibly slowed (about 2 hours). Subsequently, the mixture was filtered and after addition of a further 25 grams of the palladium catalyst hydrogenated at 6 bar to the end (2–3 hours). The mixture was filtered, the greatest part of the solvent distilled off at a water jet vacuum, and the residue treated with 8 liters of ethanol. The solution was cooled for 12 hours with flowing water and the precipitated material filtered off with suction. Then it was boiled for one hour with 2 liters of methanol with stirring and the passing through of nitrogen, allowed to cool to 25° C. and filtered off with suction. After drying in a vacuum at 55° C. there were obtained 391 grams (=94.5% of theory) of pure 7-{3-[2-(3,5-dihydroxyphenyl)-2-hydroxyethylamino]-propyl}-theophylline hydrochloride. M.P. 263°–265° C.

EXAMPLE 2

50 grams of the starting material used in Example 1 were dissolved in 0.4 liters of N-methyl pyrrolidone-(2) and after addition of 5 grams of a palladium-carbon catalyst hydrogenated at 75° C. without superatmospheric pressure. After the end of the take up of hydrogen, the product was filtered, the solvent distilled of at about 5 Torr in the water bath and the residue boiled one hour with stirring with 90% ethanol. After standing for 20 hours at 20° C. it was filtered off with suction, washed with ethanol and dried. Yield: 31 grams (=75% theory) of the product obtained in Example 1. M.P. 262°–264° C.

EXAMPLE 3

850 grams of 7-{2-[2-(3,4-dibenzyloxyphenyl)-2-oxoethyl-benzylamino]-ethyl}-theophylline hydrochloride were hydrogenated in 10 liters of dimethyl acetamide with addition of 60 grams of a 5% palladium-carbon catalyst at 5 bar hydrogen pressure and 50° C. The solvent was distilled off in a vacuum and the residue boiled for 1 hour with 8 liters of absolute alcohol with stirring and the passing through of nitrogen. After standing for 15 hours at room temperature the product was filtered with suction and again boiled with 5 liters of ethanol in the manner described above. The substance which was filtered off with suction and dried was analytically pure. There were obtained 460 grams (=89.2% of theory) of 7-{2-[2-(3,4-dihydroxyphenyl)-2-hydroxyethylamino]-ethyl}-theophylline hydrochloride. Decomposition point 186°–188° C.

The starting material for Example 3 was obtained as follows.

A solution of 643 grams of 3,4-dibenzyloxy-ω-bromacetophenone and 980 grams of 7-(2-benzylaminoethyl)-theophylline in 10 liters of toluene was boiled at reflux for 4 hours with stirring. The mixture was then cooled to 60° C., the hydrobromide formed filtered off with suction, washed with 0.5 liters of toluene and let stand for 15 hours in the cooling cabinet. The base crystallized out was filtered off with suction, suspended in methanol and converted into the hydrochloride by stirring with 230 ml of methanolic hydrochloric acid. After 10 hours it was filtered off with suction, washed with cold methanol and dried at 60° C. There were obtained 834 grams (=78.4% of theory) of 7-{2-[2-(3,4-dibenzyloxyphenyl)-2-oxoethyl-benzylamino]-ethyl}-theophylline hydrochloride having a M.P. of 170°–174° C.

What is claimed is:

1. In a process for the production of a basic substituted alkyl theophylline derivative of the formula:

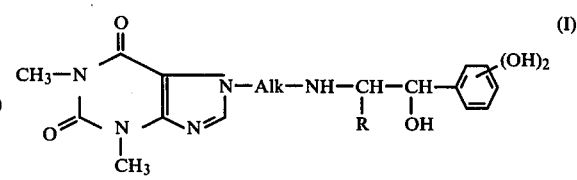

where Alk is $(CH_2)_3$, the two hydroxy groups on the benzene ring are in the 3, 4 or 3, 5 positions and R is H by catalytic hydrogenation of a compound of the formula:

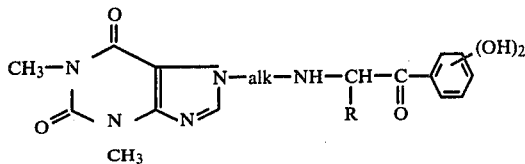

or of a compound of formula (II) wherein the two hydroxy groups on the benzene ring are in the 3, 4 or 3, 5 positions wherein the secondary basic nitrogen atom or the phenolic groups or both the secondary basic nitrogen atom and the phenolic groups contain protective groups, the improvement comprising carrying out the hydrogenation in a solvent consisting essentially of an amide formula

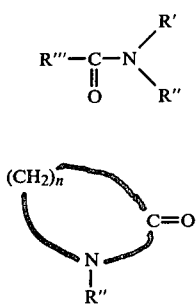

where R', R" and R'" are alkyl groups of 1 to 2 carbon atoms and n is 3 or 4 and 0 to 50% water.

2. A process according to claim 1 wherein there is present a protective group selected from the group consisting of the benzyl group, α-phenylethyl group, trityl group, p-bromobenzyl group, p-nitrobenzyl group, carbobenzoxy group, carbobenzthio group, tert.-butyl hydroxycarbonyl group, trifluoroacetyl group, phthalyl group, tert.-butylcarboxy group, p-toluenesulfonyl group, acetyl group, formyl group, propionyl group, butyryl group, carbomethoxy, carboethoxy, carbopropoxy and carbobutoxy.

3. A process according to claim 2 wherein the hydrogenation catalyst is palladium, platinum or platinum oxide.

4. A process according to claim 3 wherein the two hydroxy groups are in the 3, 5 positions.

5. A process according to claim 4 wherein the secondary basic nitrogen atom is protected by a benzyl group and the catalyst is palladium.

6. A process according to claim 5 wherein the phenolic hydroxyl groups are free from protective groups.

7. A process according to claim 6 wherein the solvent is dimethyl acetamide and has 0% water.

8. A process according to claim 7 wherein the catalyst is palladium-carbon.

9. A process according to claim 5 wherein the solvent is dimethyl acetamide and has 0% water.

10. A process according to claim 4 wherein the solvent is dimethyl acetamide and has 0% water.

11. A process according to claim 2 wherein the hydrogenation catalyst is a noble metal catalyst, the two hydroxy groups are in the 3,5-positions, the solvent is dimethyl acetamide and has 0% water and the two phenolic hydroxy groups are in the 3,5-positions.

12. The process of claim 1 wherein the amount of water in the solvent is 0–10%.

13. A process according to claim 1 wherein there is present as the solvent said amide and 0–50% of water based on the total of said amide and water by weight.

14. A process according to claim 13 wherein the solvent consists of said amide.

15. A process according to claim 1 wherein the amide is dimethyl acetamide or N-methyl pyrrolidone.

16. A process according to claim 1 wherein there is present a protective group.

17. A process according to claim 16 wherein the secondary basic nitrogen atom has attached thereto the benzyl group as the protective group.

18. A process according to claim 17 wherein the phenolic hydroxyl groups are free of protective groups.

19. A process according to claim 17 wherein both phenolic hydroxyl groups are protected by a benzyl group.

20. A process according to claim 1 wherein the hydrogenation catalyst is a noble metal catalyst.

21. A process according to claim 1 wherein the amount of solvent employed is 5 to 15 times the amount of ketone of formula (II).

* * * * *